US009579228B2

(12) United States Patent
Baradarian

(10) Patent No.: US 9,579,228 B2
(45) Date of Patent: Feb. 28, 2017

(54) INTESTINAL BARRIER SLEEVE WITH EXPANDABLE ANCHOR SECTION

(71) Applicant: Robin Baradarian, Roslyn, NY (US)

(72) Inventor: Robin Baradarian, Roslyn, NY (US)

( * ) Notice: Subject to any disclaimer, the term of this patent is extended or adjusted under 35 U.S.C. 154(b) by 0 days.

(21) Appl. No.: 14/484,828

(22) Filed: Sep. 12, 2014

(65) Prior Publication Data

US 2016/0095732 A1 Apr. 7, 2016

(51) Int. Cl.
*A61M 5/00* (2006.01)
*A61F 5/00* (2006.01)
*A61F 2/04* (2013.01)

(52) U.S. Cl.
CPC .......... *A61F 5/0079* (2013.01); *A61F 5/0076* (2013.01); *A61F 2/04* (2013.01); *A61F 5/0036* (2013.01); *A61F 2002/045* (2013.01)

(58) Field of Classification Search
CPC ........ A61F 5/0076; A61F 5/0079; A61F 2/04; A61F 2/042; A61F 2002/041; A61F 2002/043; A61F 2002/044; A61F 2002/045; A61F 2002/046; A61F 2002/047; A61F 2002/048; A61M 25/0017; A61M 25/0067; A61M 25/0074; A61M 25/0079; A61M 25/0076
See application file for complete search history.

(56) References Cited

FOREIGN PATENT DOCUMENTS

| WO | WO2011/099940 | * | 8/2011 | ............... A61F 2/04 |
| WO | WO2013/026474 | * | 2/2013 | |

* cited by examiner

*Primary Examiner* — Tatyana Zalukaeva
*Assistant Examiner* — Ariana Zimbouski
(74) *Attorney, Agent, or Firm* — Seth H. Ostrow, Esq.; Meister Seelig & Fein LLP

(57) ABSTRACT

An intestinal barrier sleeve and corresponding treatments using the sleeve are provided herein. The sleeve generally includes an expanding section coupled to a tubular section at an interface there between. The expanding section is expandable from at least a first collapsed position to at least one expanded position, where the expanding section has a conical shape that when expanded retains the sleeve in the subject gastrointestinal tract. The expanding section may further include a plurality of petal-like elements extending radially from the narrow end of the conical shape and the petal-like elements may be interconnected with a webbing to form the conical shape.

10 Claims, 4 Drawing Sheets

CLOSED SIDE VIEW

CLOSED FRONT VIEW

OPEN SIDE VIEW

OPEN FRONT VIEW

INTESTINAL BARRIER SLEEVE WITH EXPANDABLE ANCHOR SECTION

BACKGROUND OF THE INVENTION

The present application relates to devices and corresponding methods for the endoscopic treatment of obesity, diabetes, hyperlipidemia and other ailments of the digestive system.

Obesity is a growing health concern which is estimated to be directly responsible for over $147B in healthcare costs or 3%-8% of the overall healthcare costs of certain countries. Invasive therapies such as gastric bypass and stomach bands and stapling have been in use in the United States for years with limited success. In addition, such therapies often require surgical procedures, can damage the patient, and are in some cases irreversible.

A number of endoscopic therapies have been proposed for the treatment of obesity which, unlike invasive therapies, are minimally invasive and are often reversible. For instance, inflatable balloons have been inserted into the stomach to decrease the accommodation of the stomach in the hopes of creating early satiety and thus decreasing caloric intake. Similarly, intestinal barrier sleeves anchored in the small intestines have been used to decrease the absorptive surface of digestion in the small intestines with promising results. These therapies as currently in use, however, are significantly limited in their efficacy as well as safety. Indeed, the failure rate for intestinal barrier sleeves is relatively high, primarily due to patient intolerance and GI bleeding particularly at the anchorage points in the intestines.

Accordingly, there remains a need for improved endoscopic therapies for the treatment of obesity, diabetes and other ailments that are safer and more versatile than existing therapies.

SUMMARY OF THE INVENTION

In one aspect, an intestinal barrier sleeve is provided that includes an expanding anchor section coupled to a tubular section at an interface there between at one promixal end of the sleeve, the expanding anchor section expandable from at least one collapsed position to at least one expanded position, wherein in the collapsed position the expanding anchor section has a compact shape that allows the sleeve to be placed into a subject's gastrointestinal tract endoscopically and in the second position the expanded anchor section retains the sleeve in the subject's gastrointestinal tract in the stomach.

In some embodiments, the expanding section has a conical or lotus flower shape with a hole therein at a narrow end of the conical shape, and wherein the conical shape is in communication with a lumen of the tubular section through the hole. The conical shape may comprise at least one of the following specific shapes: a bowl shape, a saucer shape, a funnel shape, a trumpet shape, a bell shape, and a star shape.

In some embodiments, the expanding section comprises a plurality of petal-like elements extending radially from the narrow end of the conical shape. The expanding section may comprise a webbing, with the petal-like elements coupled to each other with the webbing.

In some embodiments, the expanding section comprises a plurality of backbone elements extending radially from the narrow end of the conical shape. In one embodiment, the expanding section further comprises a plurality of petal-like elements extending radially from the narrow end of the conical shape and wherein the backbone elements are joined to the petal-like elements. The petal-like elements are comprised of a soft, non-digestible, acid-resistant, non-abrasive plastic or rubber material.

In one embodiment, the expanding section further comprises a ring structure and wherein at least one of the petal-like elements and the backbone elements are coupled to each other via the ring structure.

In one embodiment, the tubular section is sufficiently flexible so that when the tubular section is placed such that the tubular section extends through the subject's pyloric sphincter, the sleeve will not interfere with the function of the subject's pyloric sphincter.

In another aspect, a method for treating a subject with an ailment is provided that includes the steps of: maintaining an intestinal barrier sleeve in a collapsed position, wherein the sleeve comprises an expanding section coupled to a tubular section at an interface there between, the expanding section expandable from at least the first collapsed position to at least one expanded position; placing the sleeve with the collapsing section in the first position into a subject's gastrointestinal tract endoscopically; and expanding the expanding section within the subject's gastrointestinal tract therewith retaining the sleeve in the subject's gastrointestinal tract.

In one embodiment, the sleeve is placed in the subject's gastrointestinal tract so that the expanding section is located within the subject's pyloric canal.

In one embodiment, the sleeve is placed in the subject's gastrointestinal tract so that the tubular section passes through the subject's pyloric sphincter and extends into the subject's small intestine.

In one embodiment, the tubular section is sufficiently flexible so that the sleeve will not interfere with the function of the subject's pyloric sphincter.

In one embodiment, the expanding section has a conical shape with a hole therein at a narrow end of the conical shape, and wherein the conical shape is in communication with a lumen of the tubular section through the hole.

In one embodiment, the expanding section comprises a plurality of backbone elements extending radially from the narrow end of the conical shape.

In one embodiment, the expanding section further comprises a plurality of petal-like elements extending radially from the narrow end of the conical shape and wherein the backbone elements are joined to the petal-like elements.

In one embodiment, the expanding section comprises a webbing and wherein the petal-like elements are coupled to each other with the webbing.

In one embodiment, the expanding section further comprises a ring structure and wherein at least one of the petal-like elements and the backbone elements are coupled to each other via the ring structure.

In another aspect, an intestinal barrier sleeve is provided that includes an expanding section coupled to a tubular section at an interface there between, the expanding section expandable from at least a first collapsed position to at least one expanded position, wherein the expanding section has a conical shape with a hole therein at a narrow end of the conical shape, and wherein the conical shape is in communication with a lumen of the tubular section through the hole, and wherein the expanding section comprises a plurality of petal-like elements extending radially from the narrow end of the conical shape, the petal-like elements interconnected with a webbing to form the conical shape.

Additional aspects of the present invention will be apparent in view of the description which follows.

DETAILED DESCRIPTION OF THE INVENTION

Figure 1:
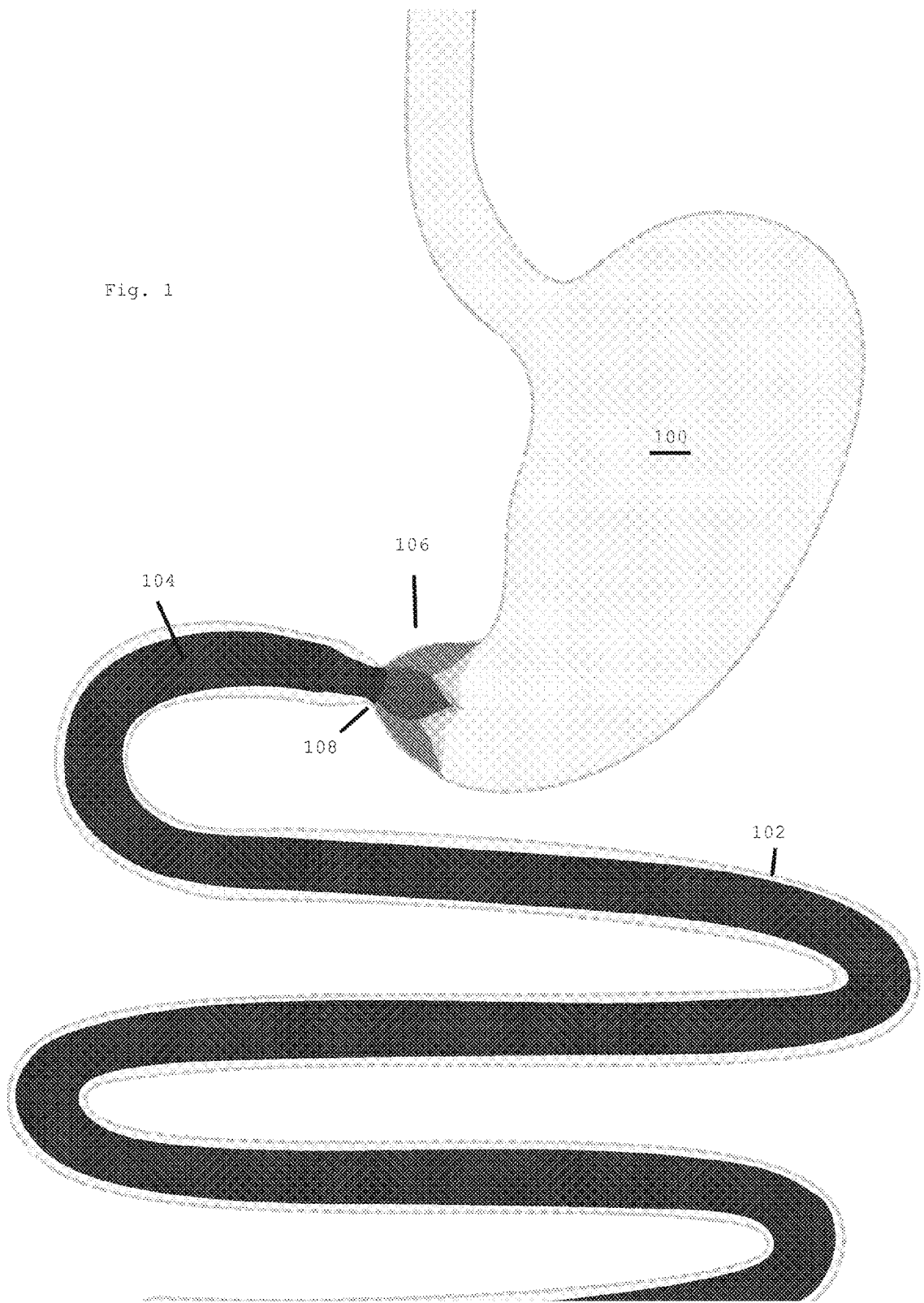
FIG. 1 is a plan view showing an intestinal barrier sleeve according to at least one embodiment of the invention in situ in a subject's gastrointestinal track.

The present application provides generally an intestinal barrier sleeve that is expandable from at least one collapsed position to at least one expanded position for placement in a subject's gastrointestinal tract. Expansion of the expandable element results in the sleeve being lodged in the subject's GI tract therewith functionally retaining the sleeve therein. Although this design allows the sleeve to be installed without the need to affix or otherwise join the sleeve directly to the GI tract, for example, with a staple or suture, the sleeve may be so attached if desired. Referring to FIG. 1, in this regard, the intestinal barrier sleeve includes an expanding section 106 coupled to an elongated tubular section 104 at interface 108. When expanded, the expanding section 106 generally has a conical shape with a hole therein at the narrow end of the conical section, which is in communication with the lumen of the tubular section 104. The type of conical shape may vary. For example, the cone may be bowl or saucer shaped, funnel shaped, trumpet shaped, bell shaped, star shaped, etc., or a combination thereof, such as a bowl-star shape as shown.

The sleeve is preferably inserted endoscopically into the subject's gastrointestinal (GI) tract so that the tubular section 104 extends through the pyloric sphincter of the subject's stomach 100 into the duodenum 102 so that the pyloric sphincter acts directly onto the tubular section 104 of the sleeve at or just below the interface 108. In this regard, the expanding section 106 and optionally the interface 108 are located within the pyloric canal of the subject's stomach 100. Once expanded, the expanding section 106 preferably provides sufficient resistance to retain the sleeve within the subject's GI tract without the need to anchor or otherwise affix the sleeve directly to the walls of the subject's GI tract. The tubular section 104 extends into the subject's small intestine an amount sufficient to reduce further digestion and/or absorption of partially digested food by the small intestine. The tubular section 104 preferably extends beyond the interface 108 by about 20 inches to about 28 inches. In this regard, the tubular section 104 is preferably impermeable with respect to partially digested foods. Also, the distal end of the sleeve (the end of the tubular farthest away from the stomach, i.e., opposite the interface 108), may be weighted with several small focal weights on the end of the sleeve itself. This may mitigate the potential retrograde migration of the sleeve.

The sleeve may be manufactured from a variety and/or a combination of biocompatible and non-biocompatible materials, such as polyester, Gortex, polytetrafluoroethyline (PTFE), polyethelene, polypropylene, polyurethane, silicon, steel, stainless steel, titanium, Nitinol, or other shape memory alloys, copper, silver, gold, platinum, Kevlar fiber, carbon fiber, etc. Where non-biocompatible materials may come into contact with the anatomic structure, the components made from the non-biocompatible materials may be covered or coated with a biocompatible material. The sleeve is preferably made in part of a biocompatible polymer sufficiently flexible to allow a user to navigate therewith though a subject's GI tract to the site of interest. Moreover, the cross section of the tubular section 104 has sufficiently thin walls so that in conjunction with the flexibility/elasticity of the material the sleeve will not interfere with the function of the subject's pyloric sphincter.

The intestinal barrier sleeve, particularly the expanding section 106 is capable of being expanded between at least two positions: a collapsed position and an expanded position. In the collapsed position (FIGS. 2-3), the expanding section 106 has a smaller profile (as compared to the expanded position (FIGS. 4-5)) for the sleeve to be located in the GI track endoscopically, for example, through a catheter. The expanding section 106 may be biased toward either position. That is, the expanding section 106 may be biased toward the expanded position so that the expanding section 106 remains expanded absent any compressive forces placed thereon. Similarly, the section 106 may be biased toward the collapsed position so that the section 106 remains collapsed absent any contrary forces. In the later, the expanding section 106 may be fixed in the expanded position against the bias using, for example, using mechanical interlocking components. Alternatively, the structure of section 106 may be deformed beyond the elastic limits of the material so that section 106 is permanently deformed into the expanded position.

Referring to FIGS. 2-5, the expanding section 106 preferably includes a plurality of petal-like elements 202, 204, 206, 208 extending radially from the narrow end of the expanding section 106. The petal-like elements may vary in shape. For example, the petal-like elements may have an almond shape, as show, an elliptical shape, a rectangular shape, etc. These shapes may have planer or concave/convex surfaces. The petal-like elements 202, 204, 206, 208 may further or alternatively include a backbone element 214 also extending radially from the interface 108. Backbone elements 214 may be straight or preferably have an arc so that the shape of section 106 conforms to the subject's anatomy at site of interest. The petal-like elements 202, 204, 206, 208 and/or the backbone thereof may further be coupled to each other via a ring structure 402. The petal-like elements 202, 204, 206, 208 and/or the backbone thereof may also be coupled to each other with webbing 216 to form the conical shaped noted above. Finally, the petal-like elements 202, 204, 206, 208 and/or the backbone thereof may terminate at the outward end in a bulbous element 210. The bulbous element 210 may be spherical, ellipsoidal, or the like. Bulbous elements 210 may also include a through hole therein.

Figure 2:
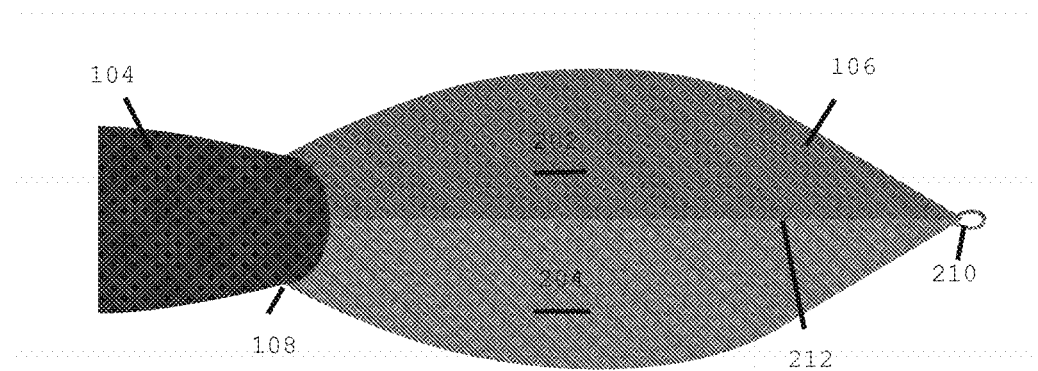
FIG. 2 is a side view of a proximal end of the intestinal barrier sleeve according to at least one embodiment of the invention with the proximal end disposed in a collapsed position.
Figure 3:
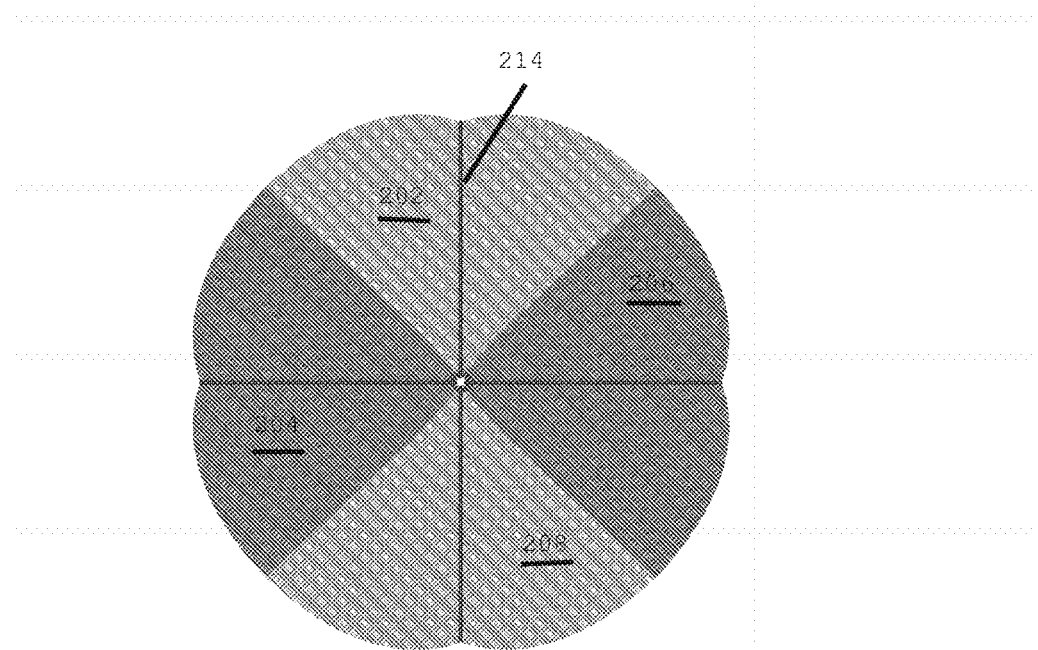
FIG. 3 is a front view of a proximal end of the intestinal barrier sleeve according to at least one embodiment of the invention with the proximal end disposed in a collapsed position.

Referring to FIGS. 2-3, the petal-like elements 202, 204, 206, 208 overlap with each in the collapsed position to allow the expanding section 106 to be placed in a compact collapsed position. In the event that section 106 is biased toward the expanded position, this collapsed position may be maintained, for example, by placing the sleeve within the lumen of a placement catheter. Other means may be used to maintain the collapsed position, including securing bulbous ends 210 to each other, for example, using the through holes therein. In these instances, expansion of section 106 in situ may be achieved by simply extruding the sleeve out from the placement catheter or otherwise removing the restrictive forces on the petal-like elements 202, 204, 206, 208 and/or the backbone thereof at the site of interest so that the spring-like elasticity of these elements causes section 106 to assume an expanded position. The sleeve is preferably just as easily removed from the site of interest endoscopically. To do so, the restrictive forces are replaced on petal-like elements 202, 204, 206, 208 and/or the backbone thereof to draw these elements together at their outward ends. This may be achieved by pulling the sleeve into the placement catheter or otherwise placing restrictive forces on the petal-like elements 202, 204, 206, 208 and/or the backbone thereof.

Figure 4:
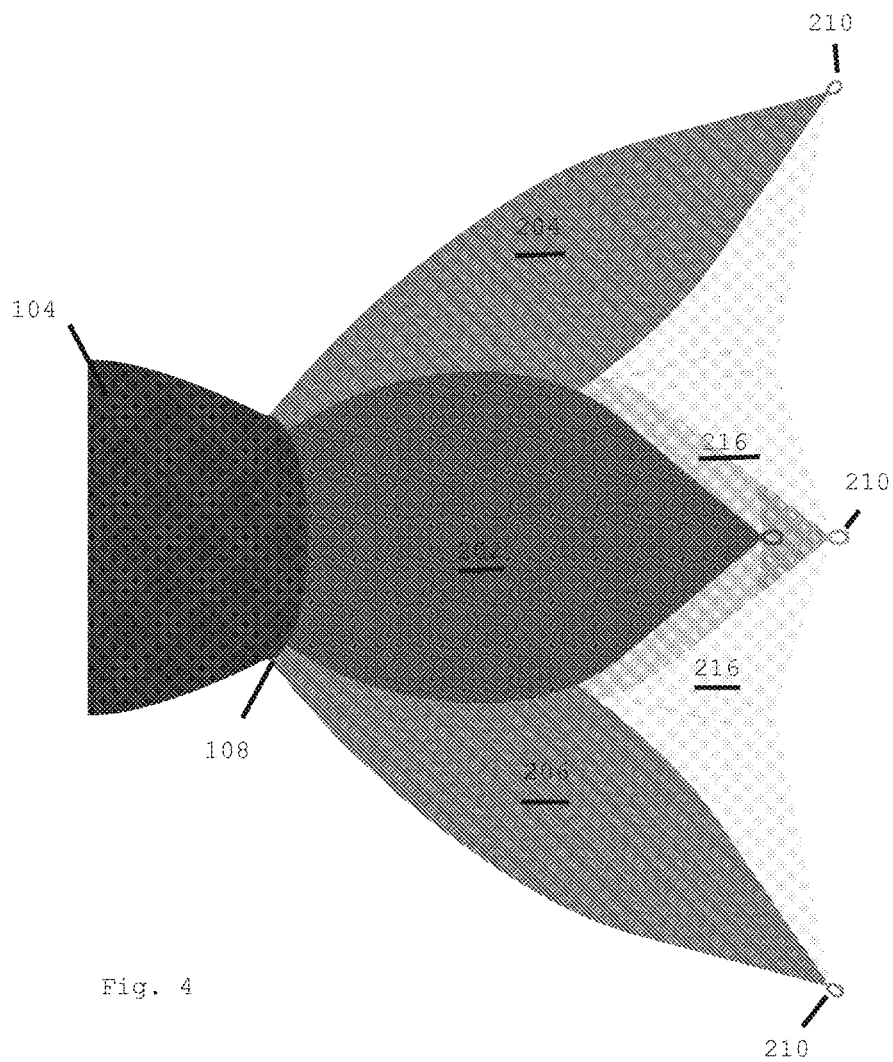
FIG. 4 is a side view of a proximal end of the intestinal barrier sleeve according to at least one embodiment of the invention with the proximal end disposed in an expanded position.
Figure 5:
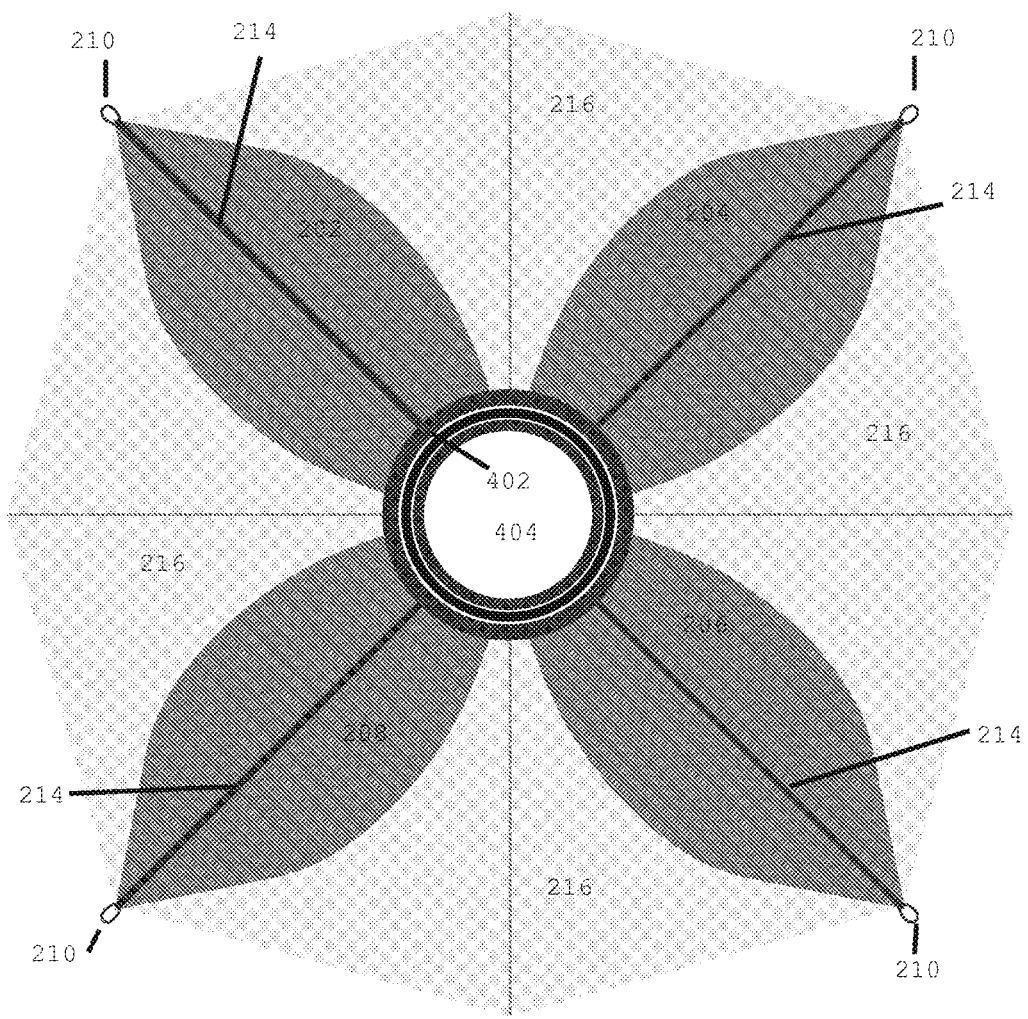
FIG. 5 is a front view of a proximal end of the intestinal barrier sleeve according to at least one embodiment of the invention with the proximal end disposed in an expanded position.

Referring to FIG. 4, the petal-like elements 202, 204, 206, 208 may partially overlap in the expanded position. As can be appreciated, the amount of the overlap will vary depending on the degree of the expansion. Specifically, the amount of the overlap will be smaller as the ends of the petal-like elements 202, 204, 206, 208 are moved farther away from each other as the expanding section 106 expands, as shown in FIG. 5. The petal-like elements 202, 204, 206, 208 and/or the backbone thereof may be hinged to the tubular member 104 at the interface 108 to facilitate the expansion/collapse of these elements.

The petal-like elements 202, 204, 206, 208 and the webbing 216 are preferably connected continuously so that there are no breaks in between in the petal-like elements 202, 204, 206, 208. This may be achieved by molding the petal-like elements 202, 204, 206, 208, the backbone 214 thereof, the webbing 216, and/or the ring structure 402 as a unit. In this instance, these individual elements may be distinguished from each other by their respective thicknesses and the resulting performance characteristics thereof. For instance, the webbing 216 may have a thickness so that it performs more like a film. That is, the webbing 216 may functionally provide a flexible, impermeable layer that allows the petal-like elements 202, 204, 206, 208 and/or the backbone thereof to move freely essentially without appreciable restriction placed thereon by the webbing 216. The petal-like elements 202, 204, 206, 208 and/or the backbone thereof on the other hand functionally provide the expanded position bias noted above and also spread the load as a result of this bias in situ on the subject's anatomy. In this regard, the dimensions of these elements (thickness and area) collectively allow the elements to provide sufficient elasticity to restrict the sleeve from unintentionally moving down the subject's GI track while also ensuring that the load placed on the subject's pyloric canal is spread sufficiently thereon to prevent or otherwise ameliorate the likelihood of any complications that may result from any excessive pressure.

The present application provides generally methods for treading ailments using the intestinal barrier sleeve(s) disclosed herein, including obesity, diabetes, as well as other ailments associated with or otherwise implicating the small intestine. These treatments may begin by preparing the subject being treated for an endoscopic procedure, which may include administering general anesthesia. The sleeve may then be passed endoscopically through the subject's GI tract so that the expanding section 106 is located in the pyloric canal of the subject's stomach and so that the tubular section 104 extends into the subject's small intestine. At this time, expanding section 106 is allowed or caused to expand, for example, by removing any restriction on section 106. For example, section 106 may be extruded out from the placement catheter used to deliver the sleeve to the site of interest. Expansion of section 106 will keep the sleeve in place until removal is desired. The design of the sleeve allows the sleeve to be removed endoscopically with relative ease. To do so, the subject is similarly prepared for the endoscopic procedure and the sleeve is removed in the reverse direction from that in which the sleeve was placed.

While the foregoing invention has been described in some detail for purposes of clarity and understanding, it will be appreciated by one skilled in the art, from a reading of the disclosure, that various changes in form and detail can be made without departing from the true scope of the invention.

What is claimed is:

1. An intestinal barrier sleeve comprising an expanding anchor section coupled to a tubular section at an interface therebetween at a proximal end of the tubular section, the expanding anchor section expandable from at least one collapsed position to at least one expanded position, wherein in the collapsed position the expanded section has a compact shape that allows the sleeve to be placed into a subject's gastrointestinal tract endoscopically and in the expanded position the expanding anchor section retains the sleeve in the subject's stomach near the gastrointestinal tract, wherein:

the expanding anchor section has a conical shape with a hole therein at a narrow end of the conical shape, and wherein the conical shape is in communication with a lumen of the tubular section through the hole;

the expanding anchor section comprises a plurality of backbone elements extending radially from the narrow end of the conical shape;

the expanding anchor section further comprises a plurality of petal-like elements extending radially from the narrow end of the conical shape and wherein the backbone elements are joined to the petal-like elements; the expanding anchor section further comprises a webbing and wherein the petal-like elements are coupled to each other with the webbing; and the expanding anchor section in the at least one expanded position provides resistance to retain the intestinal barrier sleeve within the subject's gastrointestinal tract without affixing the intestinal barrier sleeve directly to walls of the subject's gastrointestinal tract.

2. The sleeve of claim 1, wherein the conical shape comprises at least one of: a bowl shape, a saucer shape, a funnel shape, a trumpet shape, a bell shape, and a star shape.

3. The sleeve of claim 1, wherein the expanding anchor section further comprises a ring structure and wherein at least one of the petal-like elements and the backbone elements are coupled to each other via the ring structure.

4. The sleeve of claim 1, wherein the tubular section is sufficiently flexible Sc) that when the tubular section is placed such that the tubular section extends through the subject's pyloric sphincter, the sleeve will not interfere with the function of the subject's pyloric sphincter.

5. An intestinal barrier sleeve comprising an expanding section coupled to a tubular section at an interface therebetween, the expanding section expandable from at least a first collapsed position to at least one expanded position, wherein the expanding section has a conical shape with a hole therein at a narrow end of the conical shape, and wherein the conical shape is in communication with a lumen of the tubular section through the hole, and wherein the expanding section comprises a plurality of petal-like elements extending radially from the narrow end of the conical shape, the petal-like elements interconnected with a webbing to form the conical shape and further comprises a plurality of backbone elements extending radially from the narrow end of the conical shape which are joined to the petal-like elements, wherein the expanding anchor section in the at least one expanded position provides resistance to retain the intestinal barrier sleeve within the subject's gastrointestinal tract without affixing the intestinal barrier sleeve directly to walls of the subject's gastrointestinal tract.

6. The sleeve of claim 1, wherein each of the petal-like elements partially overlap with at least one other petal-like element as the expanding section is expanded to the at least one expanded position.

7. The method of claim 5, wherein each of the petal-like elements partially overlap with at least one other petal-like element as the expanding section is expanded to the at least one expanded position.

8. A method for treating a subject with an ailment, the method comprising:
   maintaining an intestinal barrier sleeve in a collapsed position, wherein the sleeve comprises an expanding section coupled to a tubular section at an interface therebetween, the expanding section expandable from at least the first collapsed position to at least one expanded position;
   placing the sleeve with a collapsing section in the first position into a subject's gastrointestinal tract endoscopically;
   expanding the expanding section within the subject's gastrointestinal tract herewith retaining the sleeve in the subject's gastrointestinal tract, wherein:
   the expanding section has a conical shape with a hole therein at a narrow end of the conical shape, and wherein the conical shape is in communication with a lumen of the tubular section through the hole;
   the expanding section comprises a plurality of backbone elements extending radially from the narrow end of the conical shape;
   the expanding section further comprises a plurality of petal-like elements extending radially from the narrow end of the conical shape and wherein the backbone elements are joined to the petal-like elements; the expanding section further comprises a webbing and wherein the petal-like elements are coupled to each other with the webbing; and the expanding section
   in the at least one expanded position provides resistance to retain the intestinal barrier sleeve within the subject's gastrointestinal tract without affixing the intestinal barrier sleeve directly to walls of the subjects gastrointestinal tract.

9. The method of claim 8, wherein each of the plurality of petal-like elements partially overlap with at least one other petal-like element as the expanding section is expanded to the at least one expanded position.

10. The method of claim 8, wherein the sleeve is placed in the subject's gastrointestinal tract so that the expanding section is located within the subject's pyloric canal.

* * * * *